United States Patent [19]
Oxley

[11] Patent Number: 5,217,443
[45] Date of Patent: * Jun. 8, 1993

[54] BIOLOGICAL FLUID SPECIMEN COLLECTION BAG

[75] Inventor: L. Thomas Oxley, Riverwoods, Ill.

[73] Assignee: T Systems Inc., Riverwoods, Ill.

[*] Notice: The portion of the term of this patent subsequent to Nov. 3, 2009 has been disclaimed.

[21] Appl. No.: 818,683

[22] Filed: Jan. 7, 1992

Related U.S. Application Data

[63] Continuation of Ser. No. 550,641, Jul. 10, 1990, Pat. No. 5,160,329.

[51] Int. Cl.$^5$ ............................................. A61M 1/00
[52] U.S. Cl. .................................. 604/317; 604/408; 604/410
[58] Field of Search ....................... 604/317-321, 604/408, 410; 206/438; 220/214

[56] References Cited

U.S. PATENT DOCUMENTS

| | | | |
|---|---|---|---|
| 3,911,918 | 10/1975 | Turner | 604/410 |
| 4,126,167 | 11/1978 | Smith | 604/317 |
| 4,183,434 | 1/1980 | Watt | 206/438 |
| 4,188,989 | 2/1980 | Andersen | 604/410 |
| 4,503,864 | 3/1985 | Powers | 604/317 |
| 4,661,100 | 4/1987 | Rechsteiner | 604/318 |
| 4,711,372 | 12/1987 | Gach | 220/214 |
| 4,865,046 | 9/1989 | Duran | 604/318 |
| 4,900,321 | 2/1990 | Kaufman et al. | 604/410 |
| 4,955,879 | 9/1990 | Mervine | 604/317 |
| 4,973,327 | 11/1990 | Goodrich, Jr. et al. | 604/408 |

FOREIGN PATENT DOCUMENTS 2176096  12/1986  United Kingdom ............ 604/317

Primary Examiner—Robert A. Hafer
Assistant Examiner—Sam Rimell
Attorney, Agent, or Firm—Reinhart, Boerner, Van Deuren, Norris & Rieselbach

[57] ABSTRACT

The invention concerns the collection of a biological fluid specimen. Both an apparatus and method of collection are described. The apparatus includes an optically transparent plastic bag having a sealable collection port. The bag may be sealed into at least two separate subcompartments. After sealing, the subcompartments are to contain substantially identical fluid specimens. The bag further includes a displaceable element for selectively dispensing and drawing fluid into the system.

37 Claims, 7 Drawing Sheets

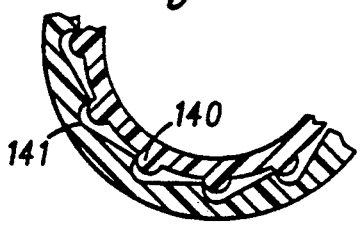
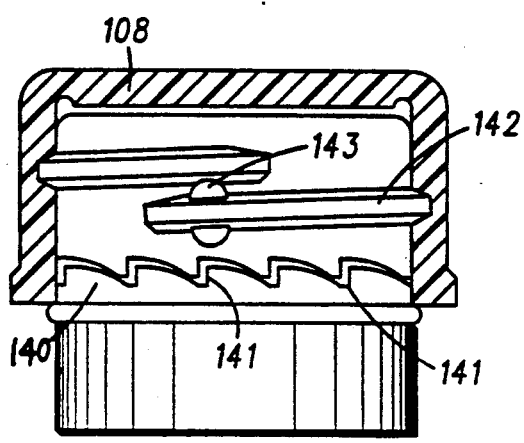
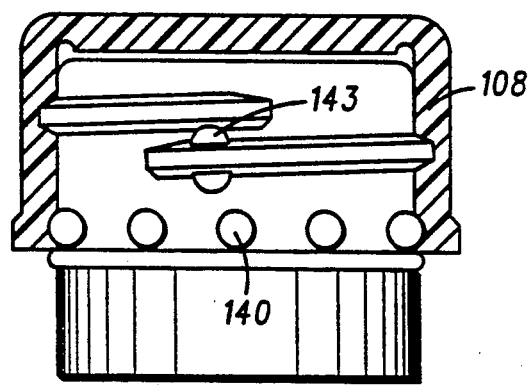
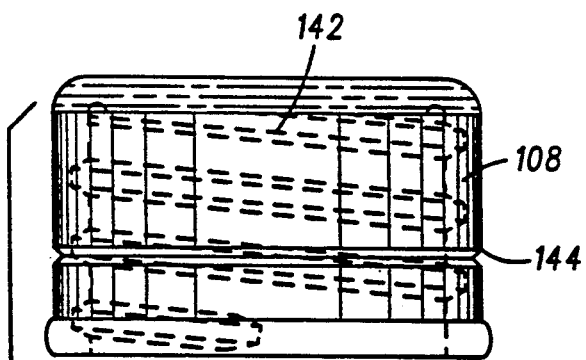
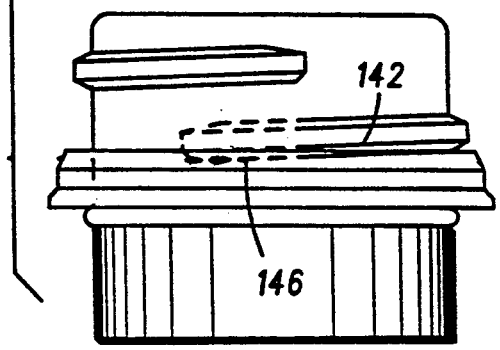

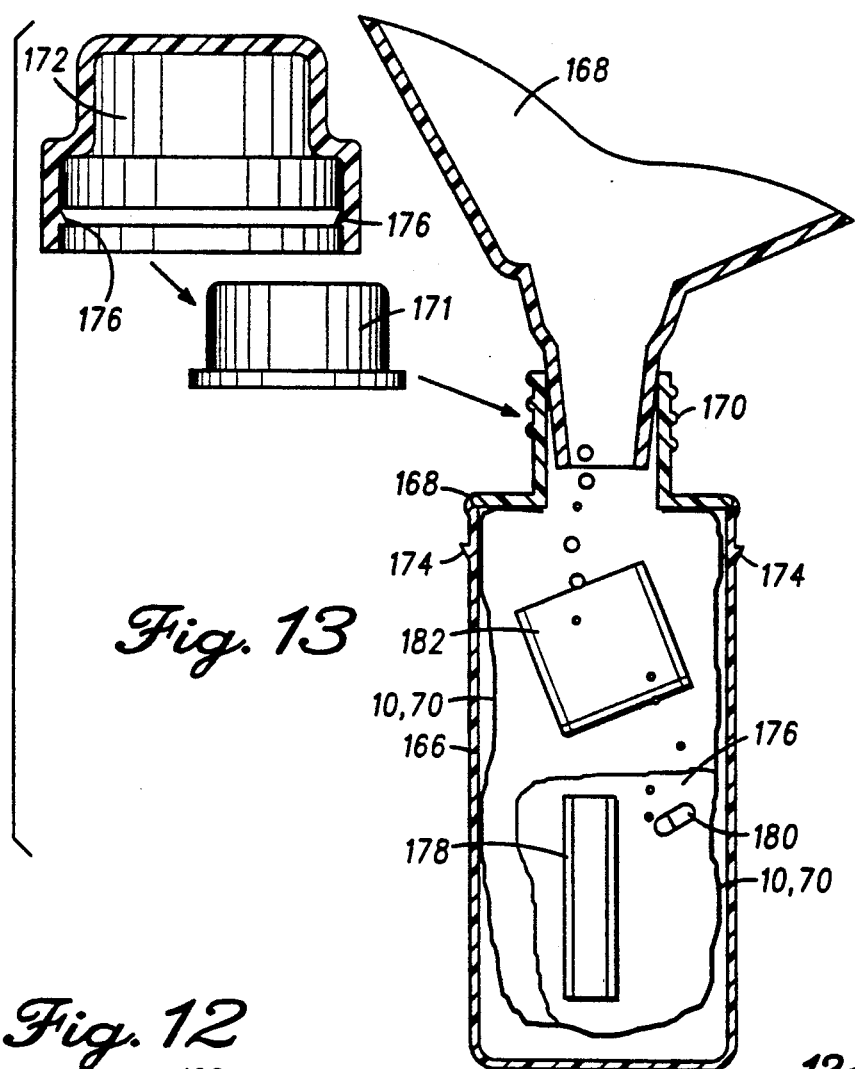
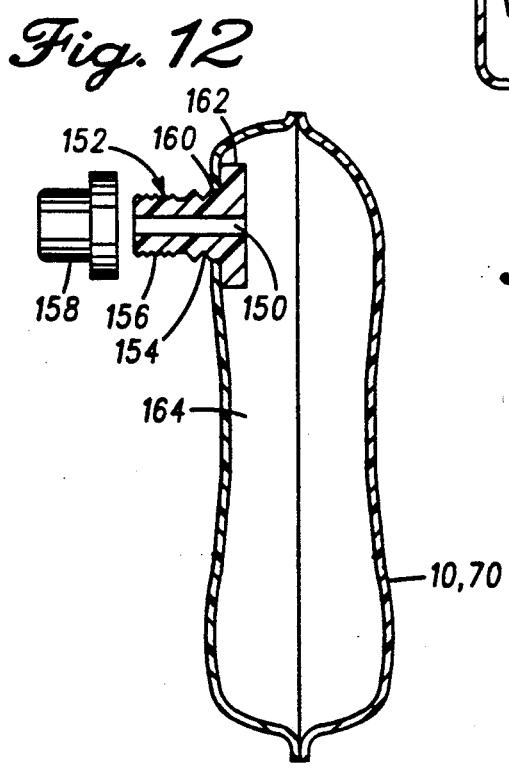
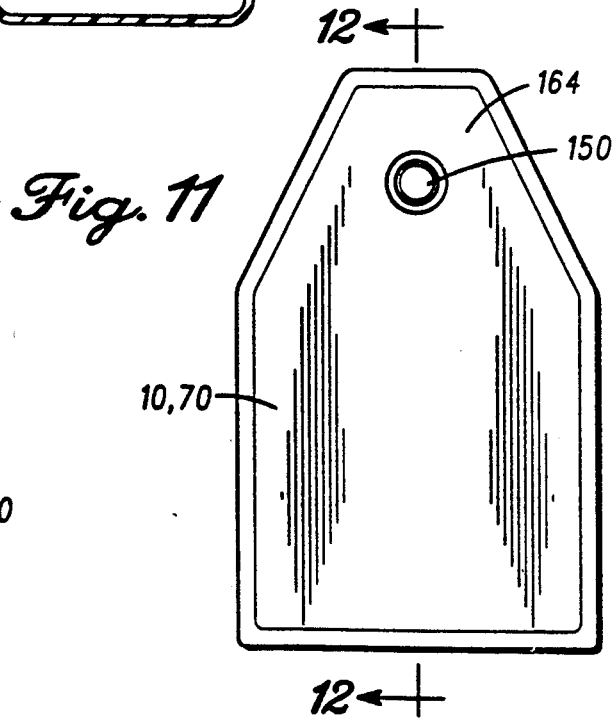

BIOLOGICAL FLUID SPECIMEN COLLECTION BAG

This is a continuation of co-pending application Ser. No. 07/550,641 filed on Jul. 10, 1990, now U.S. Pat. No. 5,160,329.

The present invention is concerned generally with a plastic bag for collection of a human fluid specimen for chemical analysis. More particularly, the invention is concerned with a system using a plastic bag for collecting urine and other biological specimens for analysis to ascertain the presence in a person of controlled drug substances or of other undesired chemicals or diseases.

Analysis for harmful drugs, diseases and other undesirable substances in a human subject involves collection and analysis of a urine or other biological liquid specimen, typically initiated by collecting the specimen in a glass or hard plastic container. Labels are attached to the exterior of the container; and a lab technician includes on the label the subject's name, date of collection and other relevant data for use in analysis of the specimen. Analysis of the specimen using such a container usually requires additional preparatory steps, including (a) creation of a new record of information for each analytical procedure performed on the specimen, while also maintaining the legal chain of evidence for the specimen, (b) physical apportionment of the initially collected specimen into a plurality of specimens for a number of different analytical evaluations, and (c) maintenance of the chemical integrity of the specimen during and after subdivision into a plurality of specimens undergoing different tests in the analytical process. There is a strong and growing demand for large scale drug testing programs and disease analysis by various corporations, governmental agencies, and particularly for military personnel, transportation workers and construction workers in high risk occupations. Such a substantial increase in the demand for drug testing programs will place a great premium on improved economics, efficiency and reliability, while requiring strict integrity of the legal chain of specimen custody.

It is therefore an object of the invention to provide an improved method and system for collecting a human fluid specimen for ascertaining the presence of controlled drug substances and diseases.

It is another object of the invention to provide a novel system for supporting a plastic bag for collecting human fluid specimens for chemical and disease control analysis.

It is a further object of the invention to provide an improved system for sealing a plastic bag used for collecting a human fluid specimen.

It is an additional object of the invention to provide a novel system for sealing and supporting a plastic bag holding a human fluid specimen collected for drug analysis.

It is still a further object of the invention to provide a novel system for collecting human fluid specimens in a plastic bag with a sealing structure permitting independent handling of the specimen in the bag without use of a basic support structure.

It is yet a further object of the invention to provide an improved system for collecting human fluid specimens using a sealing structure comprising at least one of a presealed bag and fitting unit, a plastic bag having a sealable hole around a fitting in the side of the bag, a screw on seal ring, a snap-in plug, a plug with a screw-on cap and a snap-on outer ring.

It is yet another object of the invention to provide a novel plastic bag for collecting human fluid specimens with the bag readily sealable to a sealing support structure for the independently handling and transport of the specimen.

It is an additional object of the invention to provide a novel plastic bag system for collecting human fluid specimens and sealing the fluid specimen in the bag with a tamper evident locking seal.

It is yet another object of the invention to provide an improved plastic bag system for collecting human fluid specimens while using a bag support structure which includes a transparent window for specimen inspection.

It is still a further object of the invention to provide a plastic bag system having a locking structure to prevent relative movement between the sealing elements and the plastic bag support structure.

It is still an additional object of the invention to provide an improved plastic bag adapted to receive fluid specimens from an open top or bottom having a semi rigid pipette, cuvette or test tube element and a thimble element disposed on one or both ends of the plastic bag when wrapped to form a cylindrical shape for providing additional rigidity and any tendency for the plastic bag to unfold from the cylindrical shape.

Other objects, features and advantages of the present invention will be readily apparent from the following description of the preferred embodiments thereof, taken in conjunction with the accompanying drawings described below wherein like elements have like numerals throughout the several views.

DESCRIPTION OF THE DRAWINGS

FIG. 8A shows two forms of thread structures of a sealing unit for preventing unsealing of a plastic bag once it has been sealed; and FIG. 8B illustrates a thread structure which prevents the resealing of the plastic bag once it has been unsealed;

FIG. 11 illustrates an elevation view of a side sealed plastic bag held by a fitting and support structure;

FIG. 12 shows a cross sectional view taken along 12—12 in FIG. 11; and

FIG. 13 shows a plastic bag including an outer preseal between the bag and the support fitting.

DETAILED DESCRIPTION OF PREFERRED EMBODIMENTS

Figure 1:
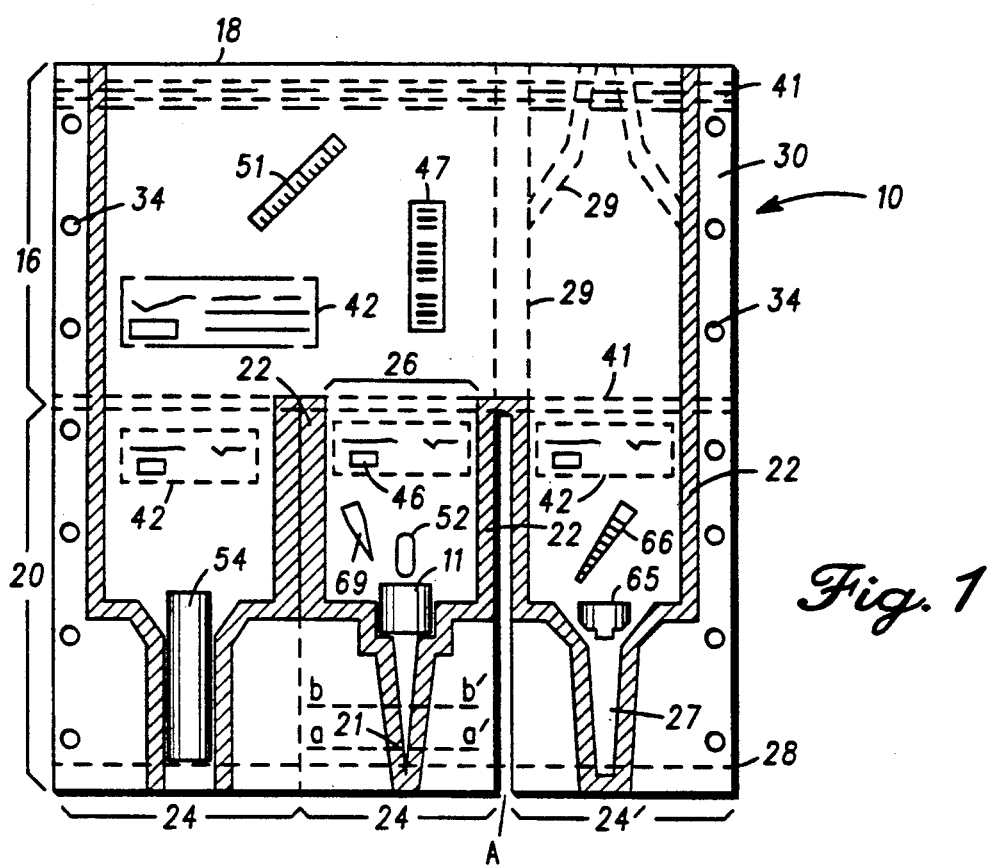
FIG. 1 is a front elevation of a multicompartment plastic bag constructed in accordance with the invention.

Referring to the drawings and in particular to FIGS. 1 and 2, a multicompartment plastic bag constructed in accordance with the invention is indicated generally at 10. Collection and analysis of a human fluid specimen is accomplished by utilizing the illustrated multicompartment plastic bag 10 (hereinafter "the plastic bag 10"). In order to carry out determination of the presence of a drug, controlled substance or disease in a person, the plastic bag 10 functions first to collect a fluid specimen taken from the subject, such as a urine specimen. Various means can be used to effectuate collection of the fluid specimen. For example, urine collection can be accomplished as shown in FIG. 3 by using a funnel 12 and container 14 having the plastic bag 10 disposed within the container 14 for receiving the urine. The plastic bag 10 includes an upper bag section 16 having an opening at one end (shown generally as 18 in FIG. 1) to enable receiving the fluid specimen. This is accomplished by inserting the plastic bag 10 into the container 14 with the open end 18 positioned at the top of the container 14. The funnel 12 is then pushed into the container 14, and the plastic bag 10 is in position to receive and accumulate the fluid specimen. Once the fluid specimen has been collected in the plastic bag 10, the funnel 12 can be removed and discarded. While the plastic bag 10 is still within the container 14, or alternatively after removal of the plastic bag 10 from the container 14, the accumulated fluid specimen can be moved within the upper bag section 16 to apportion the fluid specimen. This fluid apportionment can take place in both the upper bag section 16 and selected portions of the lower bag section 20. In the preferred embodiment the plastic bag 10 can be heat sealed at the top to preserve the specimen integrity before apportioning the specimen in the various bag sections. In an alternative embodiment one can choose to apportion the fluid specimen between the bag sections before sealing.

The ability to apportion the fluid specimen among the various bag sections enables establishing a plurality of different specimens for scientific reliability and legal requirements. The apportionment also can be useful if some prescreening tests are to be done on the fluid specimen to eliminate the need to perform complete testing on a large number of specimens.

Figure 2A:
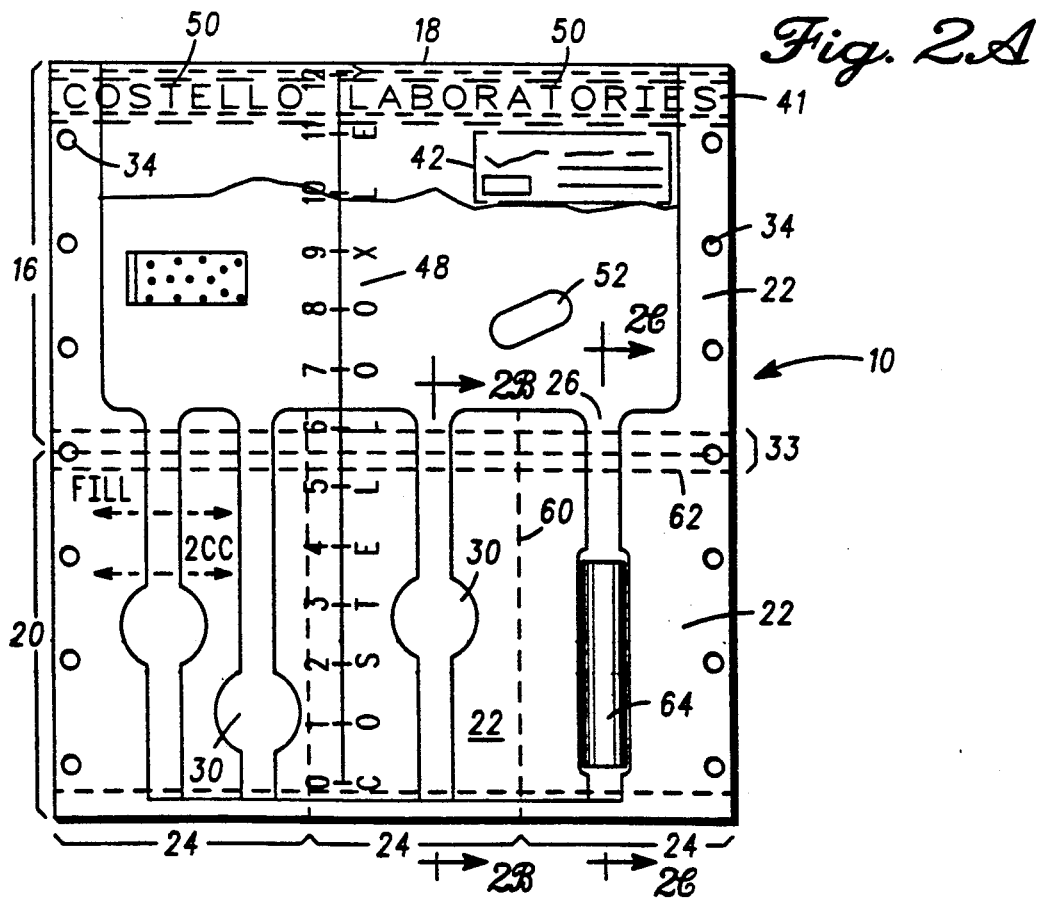
FIG. 2A illustrates a front elevation of a multicompartment plastic bag having a plurality of pouch or pocket elements.
Figure 3A:
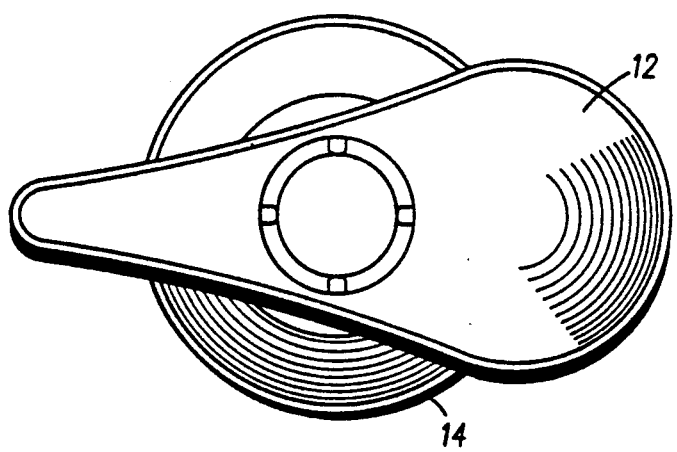
FIG. 3 shows a funnel and container holding the multicompartment plastic bag for receiving and collecting a human urine specimen.
Figure 3B:
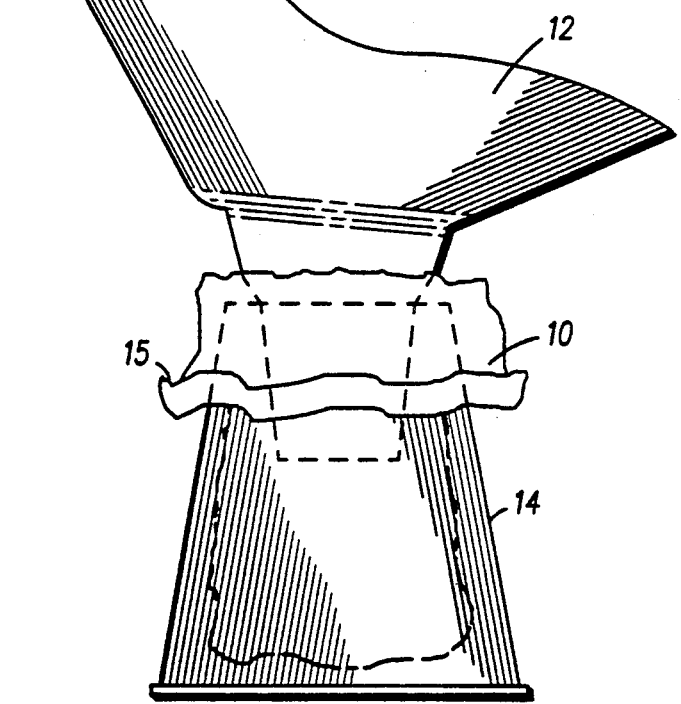

To accomplish the apportionment of the specimen within the various bag sections, the lower bag section 20 is initially at least partially open to the upper bag section 16 via opening 26 as shown in FIG. 2A once the fluid specimen is apportioned. These openings are defined by means of the location of cross-hatched seal areas 22 in the lower bag section 20 shown in FIG. 1. In the preferred embodiment these seal areas 22 have been heat sealed by the manufacturer prior to shipment to the customer and accomplished by use of any one of a variety of conventional available devices for heat sealing plastic. Thus, the bag design can accommodate various subcompartments 24 in the lower bag section 20 and provide the opening 26 between the upper and lower bag sections, 16 and 20, respectively. One can also use the seal areas 22 to provide different design configurations of subcompartments and even provide additional shapes adjunct to the subcompartments, such as a spout 27 for each of the subcompartments 24 (see FIG. 1). The spout 27 is usable by merely cutting along one line chosen anywhere above a lower seal line 28 and across the mouth of the spout 27.

In addition to the illustrated layout for the bag seal areas 22 provided by the manufacturer, the customer, or even the analytical laboratory user, can select alternative seal designs which can be implemented by various known means. A customer can thus select and prepare a custom design by using a predetermined bag size and a conventional manually operating heat sealing device 36 (see FIG. 4C) having a seal bar design in the intended geometry of the final seal areas 22. The plastic bag 10 can therefore include a plurality of different optional heat seal line patterns 29 (see FIG. 1) disposed on at least one of the plastic sheets comprising the plastic bag 10. One can, for example, use different seal line markings (dashed, dotted, and color encoded) to denote different available seal patterns. The various heat seal line patterns 29 can then be implemented by, for example, (a) using manually guided heat seal means, (b) using the heat sealing device 36 having an appropriate seal design pattern (described above) or (c) employing a conventional machine control system to perform heat seal line tracing which seals along one of the given marked seal line patterns 29.

Figure 2B:
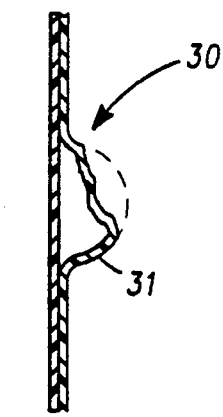
FIG. 2B is a side elevation taken along line 2B—2B of the plastic bag shown in FIG. 2A.
Figure 2C:
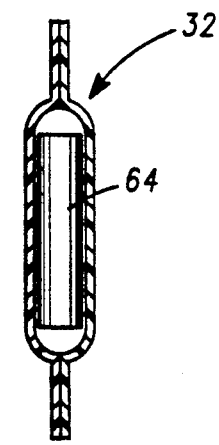
FIG. 2C is a side elevation taken along lines 2C—2C in FIG. 2A.

The ability to construct a variety of functional shapes from the plastic bag 10 can further include, for example, a pipette design 21 in FIG. 1. Once the opening 26 has been sealed to form a subcompartment 24 filled with a fluid specimen, the pipette design 21 allows dispensing small fluid specimen portions. This can be done by first cutting along the lower seal line 28 (or along lines aa' or bb' for larger openings). Tubing 11 provides support for the surrounding plastic bag 10 and enables controllably displacing fluid in the subcompartment 24 and dispensing small portions of the fluid specimen for testing. Such a pipette shape can be combined with other conceivable designs to enhance bag operation and analysis of the fluid specimen. Further useful shapes can also include, for example, a pocket or pouch element 30 in the lower bag section 20 (see FIG. 2). This pouch element 30 is defined by at least one plastic layer portion 31 being discontinuous relative to the plane of the plastic sheets of the plastic bag 10. That is, as best seen in FIG. 2B, the pouch element 30 includes the layer portion 31 which deviates from the relatively smooth surface defined by the twin sheets forming the plastic bag 10. The pouch element 30 is fillable with the fluid specimen to provide a locally enlarged specimen volume and increased specimen optical path length. This structural feature therefore allows accumulation of sufficient specimen quantities to perform analytical procedures not normally accomplishable with the relatively thin layers and unknown layer thicknesses of fluid specimens present within the plastic bag 10.

Additional functional shapes therefore allow well controlled analysis of known specific volumes and known particular optical path lengths of the fluid specimen. The analytical technician can also easily remove, by means such as a syringe or pipette, a substantial and known volume of a fluid specimen. To this end the plastic bag 10 also lends itself to inclusion of various precise volume indicators imprinted in association with the pouch element 30 (see, for example, FIG. 2A left most subcompartment 24 with the 2 cc indicate marking).

Other shapes can also be fabricated, such as a cylindrical pouch 32 (see FIG. 2C), in order to provide a fit within mating receptacles of various types of conventional analytical equipment, such as apparatus originally designed to analyze fluid specimens retained within conventional test tubes or other conventional sample containers. The cylindrical pouch 32 can further include rigid or semi rigid shapes, such as a cylindrical tube. Further details of this advantageous shape feature will be described with more particularly hereinafter.

The subcompartments 24 defined by the design of the plastic bag 10 can be selectively filled in the manner described hereinbefore: the technician can move the fluid specimen between the upper bag section 16 and lower bag section 20 and then through the openings 26 into each of the desired subcompartments 24. Either before or after the technician has apportioned the fluid specimen in the desired sections of the plastic bag 10, the conventional plastic sealing device 36 (see FIG. 4C) can be used to seal the lower bag section 20. This is accomplished by heat sealing along center seal area 33 as shown in FIG. 2A. In addition as described hereinbefore, the plastic bag 10 can be completely closed by heat sealing the upper seal area 37.

The technician can commence the specimen analysis process by separating selected ones of the subcompartments 24 and the upper bag section 16. Separation can be accomplished by, for example, cutting with scissors or separating along a prepared tear line. In another form of the invention the subcompartments 24 can be removed by merely cutting along one line since they are already separated by the manufacturer along another line (see open area denoted A for subcompartment 24 in FIG. 1).

Figure 4A:
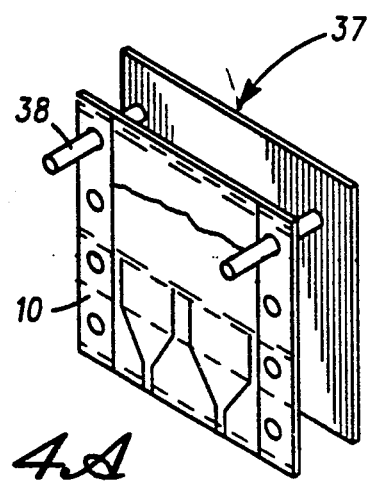
FIG. 4A illustrates a support or storage rack for holding a multicompartment plastic bag.
Figure 4B:
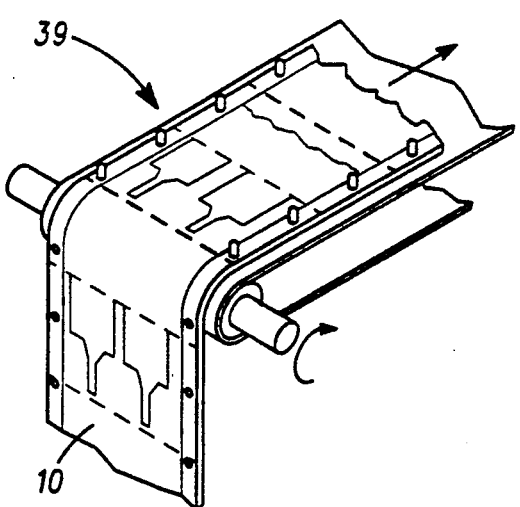
FIG. 4B shows a conveyor system for transporting the plastic bag for analysis of the fluid specimen contained therein and FIG. 4C shows a heat sealing device for closure of the plastic bag and forming selected heat seal areas on the plastic bag.
Figure 4C:
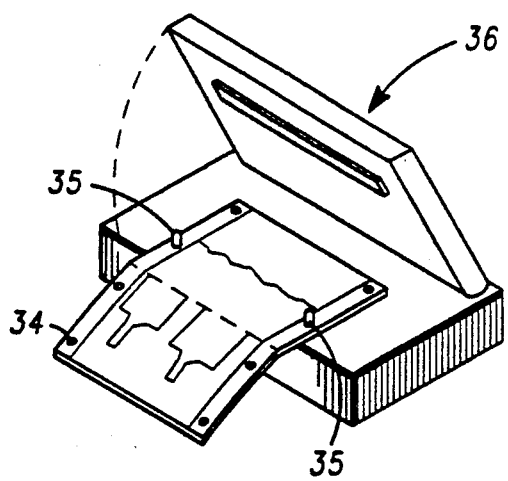

In a preferred form of the invention, the plastic bag 10 also includes holes 34 punched in the perimeter seal region 30 of the plastic bag 10 (see FIG. 1). The holes 34 can be used to assist in expediting evaluation of the fluid specimen in the plastic bag 10. For example, the plastic bag 10 can be hung on locating pins 35 of the heat sealing device 36 (see FIG. 4C). In addition, as shown in FIG. 4A the holes 34 allow hanging the plastic bag 10 on a storage rack 37 having one or more hanging rods 38 to await specimen analysis or for long term refrigerated or frozen storage. Such a storage rack 36 conserves storage space allowing large numbers of specimens to be maintained in a very small volume. The holes 34 also enable coupling of the plastic bag 10 to a conveyor system 39 for transport and subsequent analysis of the fluid specimen (see FIG. 4B).

The plastic bag 10 is preferably an optically transparent or visually translucent material allowing use of any one of a variety of conventional optical analysis procedures on the fluid specimen. Such optical analysis procedures can include, for example, simple naked eye observations and optical absorption spectrophotometry. In another form of the invention shown in FIGS. 7A and 7B, an optically transparent end cap also allows selected optical analysis to be performed. Details of this embodiment will be described hereinafter.

The plastic bag 10 and the fittings in contact with the fluid specimen also should be inert to the fluid specimen contained therein to avoid chemical modification or contamination. The plastic bag 10 should further allow long-term cold storage and freezing, while maintaining the physical and chemical integrity of the fluid specimen. Numerous conventional thermoplastic materials fulfill these requirements and examples of such materials are "Saran" coated polyester with an exterior coating of polyethylene.

As mentioned generally before, the ability to collect the fluid specimen in the upper bag section 16 and in various ones of the subcompartments 24 enables performance of a plurality of different tests and maintenance of a reference standard or reference specimen and backup standards. The upper bag section 16, for example, can be used for holding a specimen for preliminary screening or overflow. The specimens in the subcompartments 24 can, for example, be used for preliminary, primary and confirmatory analyses and also for long-term backup specimens. The ability to use numerous specimens allows a thorough analysis of the specimen. The ability to have a backup specimen(s) provides a sound evidentiary position when needed to legally and scientifically establish the presence of drugs, diseases, controlled substances or other undesirable chemicals in a human subject.

Scientific objectives for specimen analysis are met by virtue of the redundancy of available specimens, the performance of multiple specimen analyses and maintenance of a reference or backup specimen. Legal objectives are met by providing clear evidence of the identity of a specimen and unbroken chain of custody over the cycle of collection of the specimen and the performance of numerous analytical procedures. This custodial objective is accomplished in part by inclusion of an identification element on a surface of the plastic bag 10. The identification element can be, for example, a writeable area 42 for entering information identifying the specimen donor, a signature box for the donor and locations for entry of the identity and signature of each party in the chain of specimen custody. This writeable area 42 also is preferably on each of the separate sections of the plastic bag 10 in order to establish identity and custody of each specimen portion. Additional identification can be provided by other means, such as, by bar code serial numbers 46 or labels 47 attached to, or imprinted on, each of the separable bag subcompartments 24 and/or on the upper bag section 16 (see FIG. 1).

In order to prevent tampering with the fluid specimen once it has been collected, the plastic bag 10 includes a first tampering indicator means which can be an embossed or imprinted code 50 along the top seal area 37 of the plastic bag 10 (see FIG. 2A). Such a tampering indicator can be applied after collecting the specimen in conjunction with heat seal closure of the bag 10 by use of the heat sealing device 36 shown in FIG. 4C. In another aspect of the invention the tampering indicator means can extend from the upper bag section 16 to the lower bag section 20. Another such tampering indicator can be, for example, an indelible marking 48 on the plastic bag 10. The tampering indicators 48 and 50 of FIG. 2A exhibit a low symmetry design, such as, a name and a precision line having numerical or letter indicators disposed along the line. Alternatively, a more complex shape or design can be embodied in the bag sheets, such as a personalized "seal" having an appearance which would be notable altered if the plastic bag 10 were tampered with before technician analysis. As in the case of the identifying writeable areas 42, such tampering indicators can be included with each of the separate subcompartments 24 or on the upper bag section 16 in order to minimize the opportunity for any tampering occurring at any stage of the specimen analysis.

In another aspect of the invention, certain prescreening tests can be performed on the fluid specimen in order to diminish the number of "suspect" specimens which must undergo more detailed and costly analysis. Such a prescreening test can be performed on the fluid specimens collected in any of the subcompartments 24 of the plastic bag 10. As described hereinbefore in the preferred embodiment, the specimens are apportioned in the subcompartments 24 after the upper bag section 16 is sealed from the outside environment. Once the specimens are apportioned, the subcompartments 24 are sealed and isolated from each other and also from the upper bag section 16. Isolation of the various fluid specimens also enables testing to proceed wholly within the bag which also diminishes the possibility of contamination of the specimen or of disease transmission to a technician performing the analysis.

Prescreening procedures can involve simple tests, such as, checking the temperature of the fluid specimen by use of a conventional thermal strip indicator 51 (see FIG. 1) or checking pH of the specimen by the use of pH sensitive indicator strips. Rather than including the pH strips, temperature sensors or other indicators as separate components loosely disposed within the plastic bag 10, such sensors can also be integrally incorporated into the structure of the plastic bag 10, or included integrally with various means for sealing the plastic bag 10, or included integrally with various means for sealing the plastic bag 10. For example, such sensors can be incorporated with transparent windows, such as top cover 108 in FIG. 7 or as part of insert plug 115 (see FIG. 7D).

More complicated prescreening tests can involve the release of one or more analytical reagents in the upper bag section 16, such as, by opening or breaking a capsule 52 containing an analytical agent (see FIG. 2A). This analytical reagent reacts with the fluid specimen and analytical equipment (not shown) can then be used to carry out the prescreening tests. For example, Enzyme Immunoassay (EIA) can be performed by prefilling two capsules 52, one with reagent A and the other with reagent B, and sealing such capsules. At the time of specimen collection, the two capsules 52 (including the reagents A and B for determining the presence of a specific drug) are inserted into selected parts of the upper bag section 16 or the lower bag section 20. After the specimen has been collected, and the bag sections 16 and 20 sealed from one another, analysis can proceed in the selected bag section by fracturing the capsules 51.

The reagents A and B contained in each of the capsules 52 are then released to react with the fluid specimen. The reaction can generate a color change which is related to the drug concentration in the specimen. This color change can be detected through the optically transparent bag section 16 or 20, either by the naked eye or analyzed in detail by a conventional optical instrument, such as a spectrophotometer (not shown). Separate selected pairs of reagents in the capsules 52 are typically used for detecting each individual drug. Multiple ones of the subcompartment 24 can be provided in the bag sections 16 or 20, each intended for holding pairs of the capsules 52 for a different drug analysis. Alternately, a single fracturable multi-compartmented capsule 52 having numerous reagent pairs can be provided in the bag sections 16 or 20. Other conventional prescreening chemical tests are also possible, such as, for example, radio immunassay analysis, fluorescence polarization immunoassy testing or a modified thin layer chromatography option.

In another form of the invention, the plastic bag 1 further includes a substantially rigid element which can be disposed loosely in at least one particular portion of the bag. For example, the rigid element can be a piece of cylindrical tubing 54, a sample cup 65, or a conical pipette 66, as shown in FIG. 1. One can also choose to have a snug fit for the lower portion of the cylindrical tubing 54, the sample cup 65, or the conical pipette 66 in order to establish a seal to the bag 10. This seal surface will allow specimen handling such that no leakage of the fluid specimen occurs other than by a path through the tubing 54, the sample cup 65 or the pipette 66.

Figure 5:
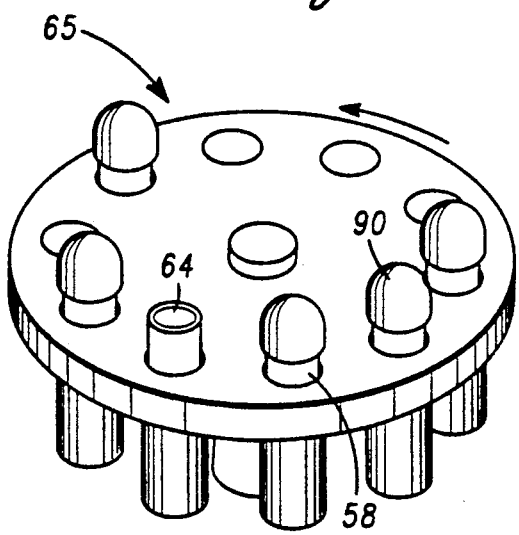
FIG. 5 illustrates a carousel style analytical apparatus having cylindrical receptacles for receiving plastic bag subcompartments including thimble elements disposed on either bag end.

Such a rigid or semi-rigid element structure advantageously also provides a predetermined shape for allowing shape sensitive mechanical handling of the fluid specimen. By establishing this predetermined shape, the specimen can be handled by analytical processes which require fitting the bag portion which holds the specimen into a mating receptacle of the analytical instrument. For example, in the case of the rigid or semi-rigid element being the cylindrical tubing 64 (see FIG. 2A), the fluid specimen is collected in the right most bag subcompartment 24 which is separated from the plastic bag 10 by cutting along seal lines 60 and 62. The separated bag subcompartment 58 containing the fluid specimen and the cylindrical tubing 54 can then be directly inserted into conventional test tube receptacles of a carousel style specimen processing station 65 (see FIG. 5). Using such an analytical processing station, an automated specimen sampling probe or syringe is lowered to retrieve a sample of the fluid specimen for chemical analysis. Therefore, the substantially rigid cylindrical tubing 64 allows the unmodified use of conventional fluid specimen processing equipment for analysis of specimens collected in the plastic bag 10 of the invention. The size and shape of the rigid element can be adjusted for the amount of fluid or biological specimen collected.

Figure 6A:
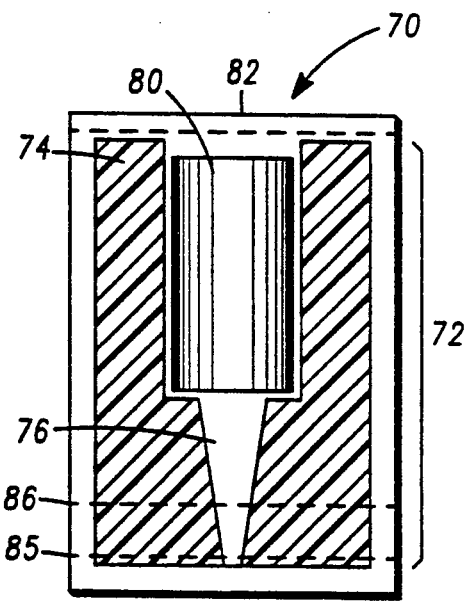
FIG. 6A shows an individual plastic bag containing a semi-rigid element.
Figure 6B:
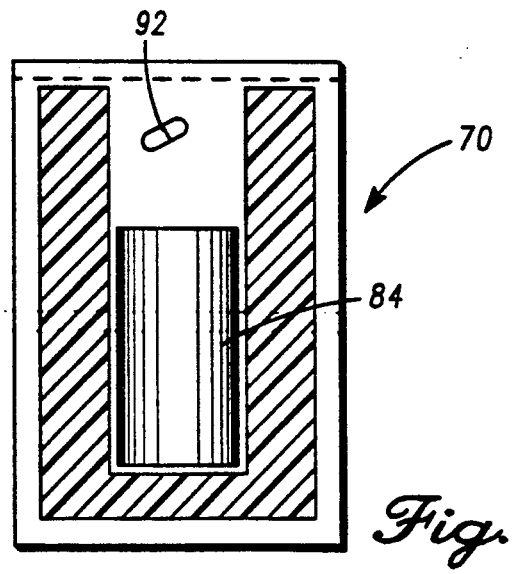
FIG. 6B illustrates an individual plastic bag containing a length of plastic tubing and FIG. 6C shows the bag of 6B with an identification label used to wrap the bag into conformity with the plastic tubing.
Figure 6C:
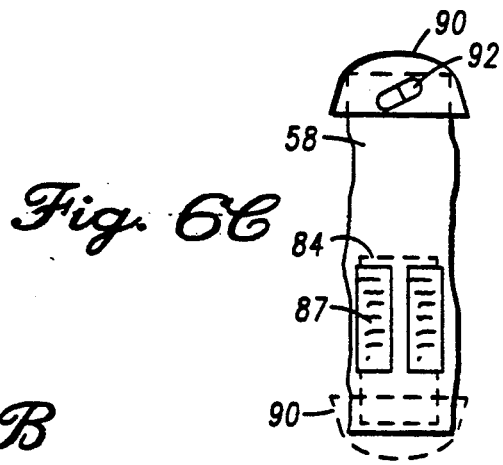

In another form of this invention, the bag subcompartment 58 can further include a thimble element 90 as shown in FIG. 6C. The thimble element 90 is shown disposed on the top end of the cylindrically wrapped bag subcompartment 58, thus providing additional rigidity and control of the cylinder shape, as well as preventing bag unwrapping and formation of unwanted air pockets in the bag subcompartment 58. The thimble element 90 can also be disposed on the bottom of the bag subcompartment 58 as shown in phantom in FIG.

6C. When disposed on the bottom, the thimble element 90 maintains the cylindrical test tube shape for use in the carousel processing station 65 (see FIG. 5).

In another aspect of the invention the multicompartment plastic bag 10 can enclose various useful tools, such as, a probe 70 in FIG. 1 for puncturing the spout of the pipette 21 to provide highly controllably release of the fluid specimen or for breaking the capsule 52 used for in situ chemical analysis.

In another form of the invention shown in FIG. 6, an individual plastic bag 70 incorporates advantageous structural elements enabling use for example, as a pipette, test tube and cuvette in fluid specimen analysis. This plastic bag 70 can be supplied individually or can be provided as a separable part of the multicompartment plastic bag 10 described hereinbefore. The structural elements included in the plastic bag 70 comprise, e.g., a pipette 72 in FIG. 6A. The pipette 72 is constructed by forming heat seal areas 74 in the plastic bag 70 to define a conical pipette section 76 and an upper pipette section 78. Within the upper pipette section 78 is disposed a semi-rigid or displaceable component, such as conventional plastic tubing 80. In the embodiment of FIG. 6A the fluid specimen is introduced through an open top 82 which is then heat sealed to enclose the fluid specimen. This fluid specimen can later be analyzed, and the technician can use the pipette 72 by cutting along one of lines 85 or 86, depending on the fluid flow rate desired. The technician can thus dispense the fluid specimen by squeezing the displaceable tube 80 causing controlled fluid removal for analysis.

The plastic bag 70 can also be presealed along the top 82, and the bottom is open to the conical pipette section 76. In such a configuration the fluid specimen can be drawn into the plastic bag 70 by squeezing the displaceable tube 80, causing a suction action drawing in the fluid specimen or other selected liquids, such as chemical reagents. The plastic bag 70 can then be sealed and subsequent specimen analysis performed.

In another feature of the plastic bag 70 a semi-rigid element, such as plastic tubing 84, can be placed within the plastic bag 70 as shown in FIG. 6B. The fluid specimen can be introduced into the plastic bag 70 which is then sealed. An identification label 87 can also be wrapped around the plastic bag 70 which is thus conformed to the shape of the semi-rigid element. In the form illustrated in FIG. 6C the plastic bag 70 takes on a cylindrical shape enabling use as a test tube type structure which can be placed into conventional test tube receptacles of automatic analysis equipment (see FIG. 5). For such analysis procedures the top of the plastic bag 70 is cut open to allow access by a syringe to remove a fluid specimen for analysis or to add test chemicals to determine the presence of selected drugs. In addition, optical testing can be performed on the fluid specimen to ascertain the presence of selected drugs. In the same manner as shown in FIG. 2A the plastic bag 70 can include a capsule 92 containing an analytical reagent for chemical evaluation and prescreening evaluation.

Figure 7A:
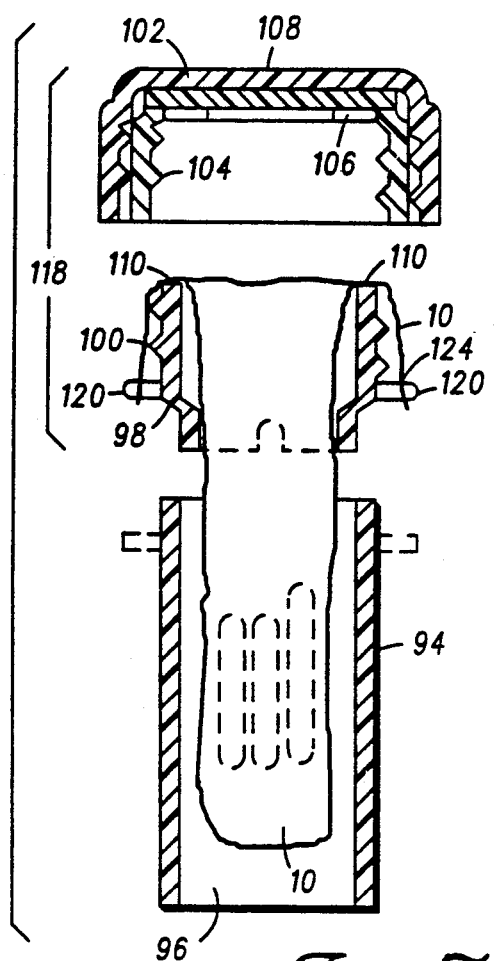
FIG. 7A illustrates a plastic bag support and sealing system in an exploded view.

In another form of the invention the plastic bag 10 (see FIG. 1) or 70 (see FIG. 6) can be held be supporting means, such as cylindrical support member 94 shown in FIG. 7A, during collection of the human fluid specimen. The plastic bag 10, 70 is inserted into the cylindrical support member 94 which can be either open or closed at distal end 96. The plastic bag 10 is then pulled through a portion of a mechanical sealing means, such as, cylindrical seal member 98, having a threaded seal portion 100 on the exterior thereof. The plastic bag 10, 70 is folded over the edge of the cylindrical seal member 98 and means for mechanically sealing is used to seal the fluid specimen inside the plastic bag 10. The mechanical sealing means can be, for example, a screw-on cap 102 which includes a threaded cap portion 104 mated to screw on the threaded seal portion 100, a top cover 108 and a seal gasket 106. The seal gasket 106 can be compressed by the screw-on cap 102 to form a seal to the top cover 108 and to seal area 110 on the cylindrical seal member 98. The top cover 108 of the screw-on cap 102 can be selected to be optically transparent enabling inspection and analysis of the fluid specimen in situ and also allow reading of a temperature sensor or pH indicator as described hereinbefore.

Figure 7B:
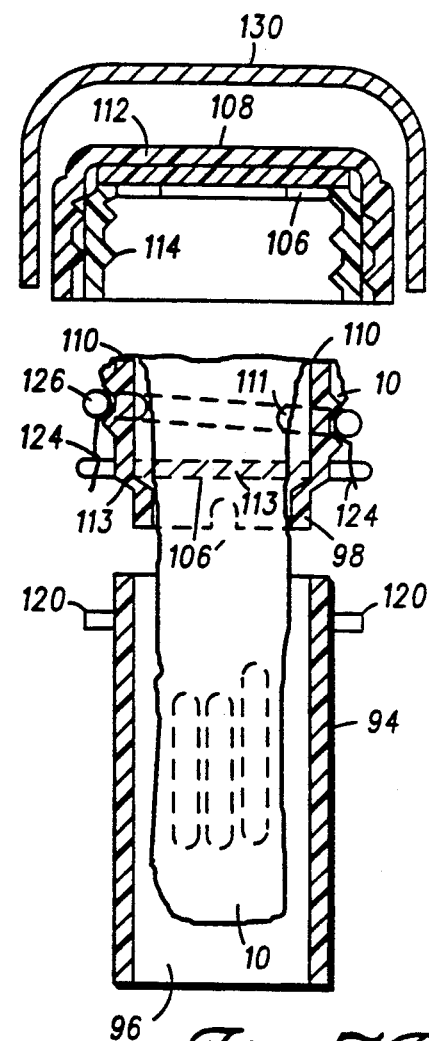
FIG. 7B shows the system of FIG. 7A including a tamper evident seal, plastic bag retention elements and an alternate bag sealing structure.

Other forms of the mechanical sealing means can also include a snap-on cap 112. As best seen in FIG. 7B, the snap-on cap 112 includes cap protrusion 114 which engages sealing protrusions 109 disposed on the exterior of the cylindrical seal member 98. Once the snap-on cap 112 is engaged, the seal gasket 106 is compressed and provides a seal both to the top cover 108 and to the seal area 110 in substantially the same manner as the embodiment shown in FIG. 7A. In another form of the invention an insert plug 115 (see FIG. 7D) is used to compress the gasket 106, which seals the plastic bag 10, 70 by forming a seal to the seal area 110 and to the insert plug 115.

Figures 7C, 7D:
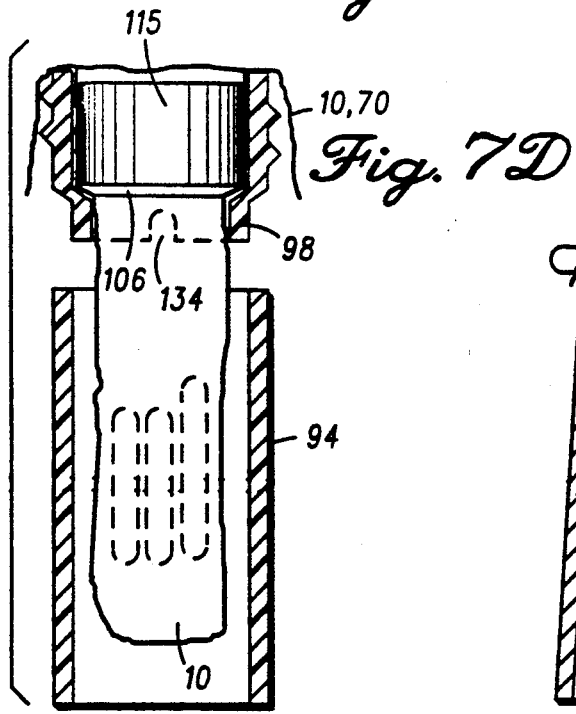
FIG. 7C illustrates a tapered sealing unit and support structure for receiving an elastic ring to retain a plastic bag.
FIG. 7D illustrates a further alternative bag sealing structure.
Figure 7E:
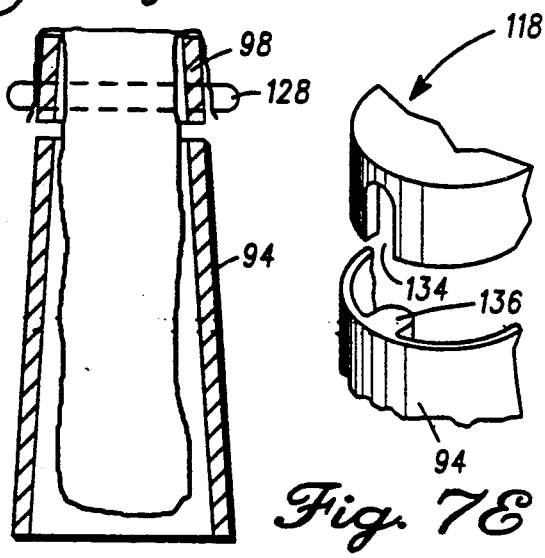
FIG. 7E shows a keyway and key element for locking relative movement of the sealing unit and support structure.

Another variation of mechanical sealing means is shown in FIG. 7D wherein the insert plug 115 is seated to compress the gasket 106 to seal the plastic bag 10, 70. In another form of the invention, the insert plug 115 can be composed of a conventional material which also performs the sealing function of the gasket 106, making a separate gasket unnecessary.

Figure 9:
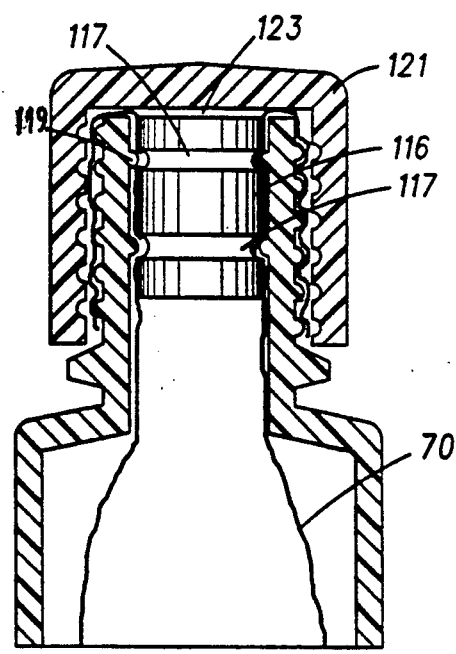
FIG. 9 illustrates a cross sectional view of a seal plug for sealing a plastic bag and insertable in the sealing position by using a screw-on cap.

An additional variation of mechanical sealing means is further shown in FIG. 9 wherein plug 116 effectuates a seal of the plastic bag 70. The plug 116 is composed of a material capable of performing a gasket or sealing function, and the plug 116 includes circumferential recesses 117 which sealingly engage inside protrusions 119 on cap 121 with the plastic bag 70 sealed between the plug 116 and the protrusions 119. The cap 121 is used to conveniently drive the plug 116 into the sealing position. In a preferred form the plug 116 further includes an attached soft disk or label 123 having a tacky adhesive material on the portion facing the cap 121. The adhesive coated label 123 thus provides a convenient coupling of the plug 116 and the cap 121, while permitting independent rotation of the cap 121 to seat the plug 116 in a sealing position.

The structure of the mechanical sealing means not only acts to seal the plastic bag 10, 70 containing the fluid specimen but also permits handling of the plastic bag independent of the support means. As shown in FIG. 7A the cylindrical sealing unit 118 is readily separated from the cylindrical support member 94. The sealed plastic bag 10, 70 and sealing unit 118 (seal member 98 and screw-on cap 102) can be easily transported by a technician to a compact storage unit (not shown). The sealing unit 118 also enables processing by an analytical technician who can conveniently gain access to selected portions of the plastic bag 10, 70 for specimen analysis. The sealing unit 118 and the plastic bag 10, 70 can also be transferred to a shortened version of the cylindrical support member 94 for storage in preparation for analysis. The disclosed mechanical sealing means has substantial versatility and can even be supported by the container 14 shown in FIG. 3 to collect the fluid specimen. The illustrated mechanical sealing embodiments also do not require use of the thermal seal unit 36 in shown FIG. 4C, which can be inconvenient and difficult to use at certain specimen collecting sites.

Figure 10B:
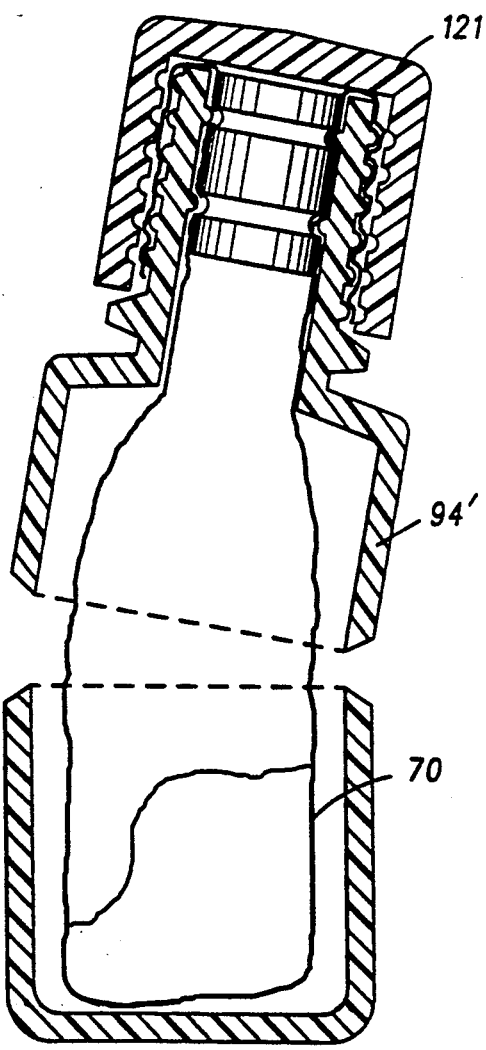
FIG. 10 shows a cross sectional view of a plastic bag support container having a breakaway feature for separating a top portion with the sealed bag attached.
Figure 10A:
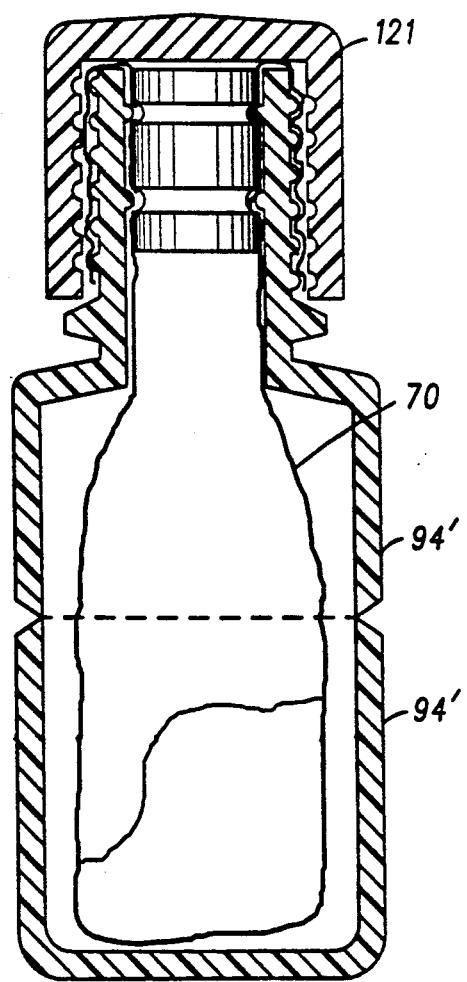

In another embodiment of the invention illustrated in FIGS. 11 and 12, any one of the mechanical sealing means shown in FIGS. 7, 9 or 10 can be used to effectuate sealing of the plastic bag 10, 70. The geometry of the plastic bag 10 in FIGS. 11 and 12 includes a hole 150 in the side of the bag. A fitting 152 can include at least one ridge and groove 154, enabling the fitting 152 to be pushed through the hole 150 of the plastic bag 10, 70. The fitting 152 can further include a threaded portion 156 which enables use of a sealing member 158 with a gasket 160 to engage and seal the plastic bag 10 at collar 162 of the fitting 152. In other forms of this basic construction, the plastic bag 10, 70 can be sealed to the collar 162 by ultrasonic welding, gluing or other such conventional fastening means. In addition, the plastic bag 10 can be presealed to the collar 162 and thus not require the gasket 160 (see for example FIG. 12 and the discussion hereinafter).

The structure shown in FIGS. 11 and 12 enables the plastic bag 10, 70 to be used for collecting the fluid specimen, and subsequently the bag can be transported without having to seal the plastic bag 10, 70 or have the donor perform any other sealing or closure operation. This feature allows the donor to carry the plastic bag 10, 70 to the technician who then seals the plastic bag 10, 70 and carries out various identification tasks. The side seal structure of the plastic bag 10, 70 also results in formation of a pocket 164 above the hole 150. Formation of this pocket 164 substantially improves the flow of the fluid specimen both into and out of the plastic bag 10, 70.

In another form of the invention shown in FIG. 13, the plastic bag 10, 70 can be presealed to the fitting 152 without requiring use of any gasket, or any screw-on cap or plug device. To accomplish this presealing, one can use ultrasonic welding or thermal sealing techniques to couple the plastic bag 10, 70 to a polypropylene or plastic form of the fitting 152. Also note in FIG. 13 the plastic bag 10, 70 is disposed in the more typical open top geometry rather than the side sealable version shown in FIGS. 11 and 12. This presealing feature can also be used for the side seal geometry.

As illustrated in FIG. 13, cylindrical support member 166 includes snap-on top portion 168 which acts to secure fitting 170 to the member 166. Once the plastic bag 10, 70 and the connected fitting 170 have been coupled to the cylindrical member 166, the donor can insert a collection funnel 168 and collect the fluid specimen in the plastic bag 10, 70. The donor then can transport the fluid specimen to a technician who can install tamper cap 171 and protective top cover 172. The tamper cap 171 is substantially the same as shown in FIG. 8 and functions in the manner described hereinafter. The protective top cover 172 is then placed over the tamper cap 171 and lockingly engaged to the cylindrical member 166 by cooperation between a protruding outside flange 174 on the member 166 and a protruding inside flange 176 on the top cover 172. The firmly attached top cover 172 provides further protection for the fluid specimen in the plastic bag 10, 70. Such a construction minimizes the concern of fluid spillage or damage to the plastic bag during transport, or when the fluid specimen is mailed to a distant testing laboratory.

The plastic bag 10, 70 shown in FIG. 13 can include subcompartment 176 constructed and used in the same manner as described hereinbefore. Within the subcompartment 176 can be any one of the various implements such as the cylindrical vial 178 or the breakable capsule 180 used in the manner discussed previously. In addition, the plastic bag 10, 70 can include a preformed plastic pocket 182 disposed on the exterior of the bag with the plastic pocket 182 openable for storing and removal of informational materials.

In another embodiment the plastic bag 10, 70 can be held on the cylindrical support member 94 by retention means. The retention means enables easy and reliable transport to the technician by the donor of the collected fluid specimen and with the technician then sealing the plastic bag 10, 70. Retention means can include, for example, retention posts 120 disposed on the exterior of either the sealing unit 118 or the cylindrical support member 94 (see in phantom on FIG. 7A). The plastic bag 10, 70 includes mating holes 124 which slip over the retention posts 120 thereby holding the plastic bag 10, 70 until sealed by the technician. Such an arrangement helps insure the fluid specimen is not spilled before the plastic bag 10, 70 is sealed.

Another reliable form of retention means can include a separable form of the cylindrical support member 94' as shown in FIG. 10. On the left is shown the support member 94' having a scoring line or concave recession 95 which provides a line along which separation can be effected. The scoring line 95 allows removal of the upper portion of 94' supporting the plastic bag 10, 70 as shown in the right view of FIG. 10. The separated sealed fluid specimen can then be more conveniently stored and readily accessed by the technician who will perform testing of the fluid specimen.

An additional form of retention means can include an elastic ring 126 which abuts and retains the fold over portion of the plastic bag 10, 70 in the manner shown in FIG. 7B. Another form of retention means can be a tapered form of either the cylindrical support member 94 or the sealing unit 118. One such form of retention means has a smaller diameter at the top compared to the distal end (see FIG. 7C). A slip ring 128 can then be placed into a snugly fitted position with the member 94, or as shown in FIG. 7C fitted onto the cylindrical seal member 98 thereby retaining the plastic bag 10, 70 in position.

Another feature of the embodiment of FIG. 7 is locking means for preventing movement of the sealing means relative to the support means. For example, in FIG. 7E is shown a keyway 134 in the sealing unit 118 and a mating key element 136 disposed on the cylindrical support member 94. Upon engaging the key element 136 with the keyway 134, relative rotation of the sealing unit 118 and the member 94 is prevented. This is particularly important when trying to seal the plastic bag 10, 70 using the threaded cylindrical seal member 98 and threaded seal portion 100 shown in FIG. 7A. A good seal would be difficult to achieve without such a locking means.

In a manner similar to the embodiments illustrated in FIG. 2A a tamper evident seal 130 can also be attached to the top of the seal cap 10B to ensure the fluid specimen is not adulterated or modified prior to analysis (see exploded view of FIG. 7B).

Tampering with the fluid specimen can also be discouraged by using a thread design for the mechanical sealing means which allows sealing of the plastic bag 10, 70 but either does not permit unsealing in any manner via the threaded portion or does not permit unsealing of the plastic bag 10, 70 without destruction of the sealing means. For example, as seen in FIG. 8A, several forms of circumferential obstacle structures 140 prevent turning of the cap 108 in any direction other than the sealing direction. As the cap 108 is turned to seal the plastic bag; recesses 141 along the cap periphery matingly engage the obstacle structure 140 which prevents any attempt to unseal the plastic bag. In another approach shown in FIG. 8B to preventing tampering with the fluid specimen, the threads 142 have thread contours which allow sealing, however, upon unsealing easily recognizable damage is caused to the threads 142 by breaking away of a thin wall, cap ring 144. Thus, the accompanying damage to the adjacent inside threads 146 will prevent sealing after being unsealed. As a consequence, for purposes of analyzing the fluid specimen, the technician must access the fluid specimen in the plastic bag 10,70 in another manner, making unauthorized unsealing and tampering more difficult. While preferred embodiments of the invention have been shown and described, it will be clear to those skilled in the art that various changes and modifications can be made without departing from the invention in its broader aspects as set forth in the claims provided hereinafter.

What is claimed is:

1. A method of processing a human fluid specimen solely for analysis, comprising the steps of:
   collecting said human fluid specimen in a sealable container;
   sealing said container with said specimen therein using nonreusable seals; and
   further sealing said container into at least two compartments by sealing means resulting in said completely sealed compartments containing redundant, substantially homogeneous forms of said human fluid specimen collected solely for said analysis.

2. The method as defined in claim 1 further including the step of performing an analytical test by contacting said human fluid specimen with an analytical agent after collection of said human fluid specimen.

3. A method of processing a human fluid specimen solely for analysis, comprising the steps of:
   collecting said human fluid specimen in a sealable container having at least one displaceable element means;
   sealing said container with said specimen therein into at least two compartments by sealing means resulting in said completely sealed compartments containing redundant, substantially homogeneous forms of said human fluid specimen collected solely for said analysis; accessing said human fluid specimen in said container; and
   displacing said displaceable element means of said container in order to selectively dispense and draw into said container said human fluid specimen.

4. The method as defined in claim 3 further including the step of contacting said human fluid specimen with test means for analyzing said specimen.

5. The method as defined in claim 4 wherein said test step comprises at least one of opening a capsule contacting an analytical agent with said human fluid specimen after collection and contacting an indicator strip with said specimen.

6. A method of optically analyzing a human fluid specimen, comprising the steps of:
   collecting said human fluid specimen in a sealable container having a collection port with said container made of a plastic material allowing optical analysis of said specimen held within said container;
   sealing said collection port;
   sealing said container into at least two compartments using nonreusable seals resulting in sealed compartments containing redundant, substantially homogeneous forms of said human fluid specimen collected solely for analysis purposes; and
   optically inspecting said human fluid specimen for chemical analysis characterization.

7. The method as defined in claim 6 wherein said step of optically inspecting comprises performing spectroscopy on said human fluid specimen.

8. A method of processing a human fluid specimen in a flexible, plastic system which allows optical inspection comprising the steps of:
   collecting solely for analysis said human fluid specimen in said flexible, plastic system having a collection port and further including at least one displaceable element means allowing displacement of said human fluid specimen in said system made of plastic material allowing optical inspection of said human fluid specimen contained therein;
   sealing said flexible plastic system using nonreusable seals and forming at least two compartments in said system resulting in said sealed compartments containing redundant, substantially homogeneous forms of said human fluid specimen collected solely for analysis;
   opening an access port for removal of said human fluid specimen; and
   displacing said system using said displaceable element means to selectively dispense and draw in said human fluid specimen through said access port.

9. The method as defined in claim 8 further including the step of optically inspecting said human fluid specimen.

10. The method as defined in claim 9 wherein said optical inspection step comprises contacting said human fluid specimen with at least one of an analytical agent or test indicator strip and visually examining the color of said tested specimen.

11. The method as defined in claim 9 wherein said optical inspection step comprises performing spectroscopy on said human fluid system.

12. A collection and analysis system for a human fluid specimen collected solely for analysis, comprising:
   a container for accumulating said human fluid specimen, said container having at least one collection port allowing the input of said human fluid specimen and further including means for sealing said collection port after collection of said human fluid specimen and after collecting said human fluid specimen said container is sealable into at least two subcompartments containing redundant, substantially homogeneous forms of said human fluid specimen collected solely for said analysis; and
   at least one access port allowing controlled dispensing from at least one of said subcompartments of said human fluid specimen for said analysis, said system further including at least one displaceable element means for displacing said container in order to selectively dispense from and draw into said container for performing said analysis or said human fluid specimen.

13. A collection and analysis system for a human fluid specimen collected solely for analysis purposes, comprising;
   a plastic container for accumulating said human fluid specimen, said plastic container having at least one collection port allowing the input of said human fluid specimen and after collecting said human fluid specimen said plastic container is sealable by means for mechanically sealing said collection port and said plastic container further sealable into at least two subcompartments by sealing means resulting in said sealed subcompartments containing redundant, substantially homogeneous forms of said human fluid specimen collected solely for said analysis purposes; and
   at least one displaceable element means for displacing said plastic container in order to selectively dispense from and draw into said container for performing analysis on said human fluid specimen.

14. A collection system permitting optical and/or chemical analysis of a human fluid specimen collected solely for analysis purposes, comprising:
   a flexible plastic container having a collection port allowing collection of said human fluid specimen therein and after collecting said human fluid specimen said plastic container is sealable into at least two subcompartments by sealing means resulting in sealed subcompartments containing redundant, substantially homogeneous forms of said human fluid specimen collected solely for said analysis purposes;
   test means for chemically testing said human fluid specimen and disposed within said system; and
   means for mechanically sealing said collection port with said collected human fluid specimen included in said collection system, said flexible plastic container further allowing optical inspection of said human fluid specimen in said container.

15. The collection system as defined in claim 14 wherein said test means comprises at least one of a chemical test and an analytical reagent disposed within said system and activated for testing after collection of said human fluid specimen.

16. A collection system of separable subcompartments for holding a human specimen collected solely for analysis allowing independent specimen characterization, comprising:
   a sealable container for accumulating said human specimen, said container having at least one collection port allowing the input of said human specimen and further including means for sealing said collection port after collection of said human specimen;
   said container sealable into at least two of said separable subcompartments by sealing means resulting in sealed subcompartments containing redundant, substantially homogeneous forms of said human specimen solely for analysis allowing independent specimen characterization; and
   said sealable container further including at least one access port allowing the controlled dispensing of said human specimen from at least one of said subcompartments of said container for said analysis, said container further including at least one type of displaceable element means for displacing in order to selectively dispense and draw into said system said human specimen.

17. A collection system with a plurality of subcompartments for a human specimen collected solely for analysis purposes allowing independent specimen characterization, comprising:
   a plastic container for accumulating said human fluid specimen, said plastic container having at least one collection port allowing the input of said human specimen and after collecting said human specimen said plastic container sealable by means for sealing said collection port and said plastic container further sealable into at least two of said subcompartments by sealing means resulting in said sealed subcompartments containing redundant, substantially homogeneous forms of said human specimen allowing the independent specimen characterization of said redundant specimens collected solely for analysis purposes; and
   displaceable element means for displacing in order to selectively dispense from and draw into said container for performing analysis on said human specimen.

18. An optically transparent collection system for holding a human specimen collected solely for analysis purposes with a plurality of subcompartments allowing independent, redundant specimen characterization, comprising:
   said optically transparent collection system comprised of optically transparent, flexible plastic and having at least one collection port allowing the input of said human specimen and after collecting said human specimen said plastic collection system is sealable into at least two of said subcompartments by sealing means resulting in sealed compartments containing redundant, substantially homogeneous forms of said human specimen allowing the independent, redundant specimen characterization during the analysis;
   test means disposed within a portion of at least one of said subcompartments; and
   means for sealing said collection port with said collected human specimen contained within said system and said optically transparent plastic allowing said human specimen to be optically examined while held in said collection system.

19. The optically transparent collection system as defined in claim 18 wherein said optically transparent plastic comprises a visually translucent plastic.

20. The system as defined in claim 18 wherein said flexible plastic comprises a plastic coating consisting essentially of a polyethylene.

21. The system as defined in claim 18 further including an optical analysis system for performing optical measurements on said human specimen in said system.

22. The system as defined in claim 18 wherein said test means comprises at least one of an analytical agent, a thermal indicator, a pH indicator and a chemical test element.

23. The system as defined in claim 18 wherein said test means is integrally incorporated into a portion of said collection system.

24. The system as defined in claim 23 wherein said test means is incorporated into said means for sealing portion of said collection system.

25. The system as defined in claim 23 wherein said test means is incorporated into a visually transparent window portion of said optically transparent collection system.

26. The system as defined in claim 25 wherein said optically transparent collection system aside from said visually transparent window is visually translucent.

27. The system as defined in claim 18 wherein said test means comprises an analytical agent selectively released for testing of the human specimen after collection thereof.

28. The system as defined in claim 27 wherein said analytical agent comprises a capsule openable by a technician for release of said analytical agent testing of said human specimen after collection and sealing in said system.

29. The system as define in claim 28 wherein said analytical agent consists of at least one of a two capsule means for containing analytical agents and a multicompartment capsule of different agents opened by the technician for release of said analytical agent for testing of said human specimen.

30. The system as defined in claim 28 wherein said analytical agent comprises a chemical test means.

31. The system as defined in claim 18 wherein one of said subcompartments containing said test means is separated from said system and said human specimen tested.

32. The system as defined in claim 31 wherein said subcompartment further includes a displaceable element means for displacing in order to selectively dispense and draw into said subcompartment for performing analysis on said human specimen.

33. A collection system for a human fluid specimen collected solely for analysis purposes, comprising:
a plastic container for accumulating said human fluid specimen, said plastic container having at least one collection port allowing the input of said human fluid specimen and after collecting said human fluid specimen said plastic container is sealable into at least two subcompartments by sealing means resulting in sealed subcompartments containing redundant, substantially homogeneous forms of said human fluid specimen collected solely for said analysis purposes; and
means for mechanically sealing said collection port of said plastic container with said fluid specimen therein and further comprising means for supporting said plastic container during collection of said human fluid specimen and comprises a port fitting coupled to said plastic container and said sealing means engaged with said port fitting.

34. The collection system as defined in claim 33 wherein said plastic container comprises a plastic coating consisting essentially of polyethylene.

35. A collection and analysis system for a human fluid specimen collected for analysis, comprising:
a container system for accumulating said human fluid specimen, said container system having at least one collection port allowing the input of said human fluid specimen and further including means for sealing said collection port after collection of said human fluid specimen and said container system further being sealable into at least two compartments after collecting said human fluid specimen, said container system being separable into at least two separate compartments containing redundant, substantially homogeneous forms of said human fluid specimen collected for analysis; and
at least one access port allowing controlled dispensing from at least one of said compartments of said human fluid specimen for analysis, said collection and analysis system further including at least one displaceable element means for displacing said container system in order to selectively dispense from and draw into said container system for performing said analysis of said human fluid specimen.

36. A flexible, plastic multicompartment system for processing a human fluid specimen and which allows optical inspection of said human fluid specimen, comprising:
at least one collection port said flexible plastic system;
said flexible, plastic form at least two compartments in said system resulting in said sealed compartments containing redundant, substantially homogeneous forms of said human fluid specimen collected solely for analysis;
at least one access port for removal of said human fluid specimen; and
displaceable element means for selectively dispensing and drawing in said human fluid specimen through said at least one access port.

37. A plastic container system for selectively collecting and dispensing and enabling the analytical testing of a biological fluid specimen, comprising:
at least one sealable plastic container in said system having an opening to receive said fluid specimen and at least one compartment in said container;
at least one access port in said plastic container for removal of said fluid specimen; and
displaceable element means for selectively dispensing and drawing in said fluid specimen through said access port of said plastic container.

* * * * *